United States Patent
Buysch et al.

(10) Patent No.: US 6,175,017 B1
(45) Date of Patent: Jan. 16, 2001

(54) PROCESS FOR THE PRODUCTION OF ARYL CARBONATES

(75) Inventors: Hans-Josef Buysch; Norbert Schön; Günther Jeromin, all of Krefeld (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 08/108,854

(22) Filed: Aug. 18, 1993

Related U.S. Application Data

(63) Continuation-in-part of application No. 07/780,494, filed on Oct. 22, 1991, now abandoned.

(51) Int. Cl.$^7$ .................. C07D 23/79; C07D 307/02; C07C 68/00; C07C 43/162
(52) U.S. Cl. .................. 546/302; 558/280; 558/281; 558/282; 549/478
(58) Field of Search .................. 558/280, 281, 558/282; 546/302; 549/478

(56) References Cited

U.S. PATENT DOCUMENTS

| | | | |
|---|---|---|---|
| 2,837,555 | 6/1958 | Lee | 558/274 |
| 3,234,263 | 2/1966 | Kurkly et al. | 558/274 |
| 3,864,365 | * 2/1975 | Grosse et al. | 552/7 |
| 4,012,406 | 3/1977 | Buysch et al. | 558/274 |

FOREIGN PATENT DOCUMENTS 2161254   6/1973   (DE) .................................... 558/274

OTHER PUBLICATIONS

Fieser annd Fieser, "Reagents for Organic Synthesis" vol. 1, pp. 15, 40, 109, 182 and 408, Wiley pub. (1967).*

Fieser and Fieser, "Reagents for Organic Synthesis," vol. 3 p. 145, Wiley Pub. (1972).*

* cited by examiner

*Primary Examiner*—Alan L. Rotman
(74) *Attorney, Agent, or Firm*—Joseph C. Gil; Aron Preis

(57) ABSTRACT

A process for the preparation of carbonates containing aromatic ester groups is disclosed. The process entails reacting aromatic monohydroxy componds with phosgene or with chlorocarbonic acid esters of aromatic monohydroxy compounds at a temperature of 50 to 350° C. and in the presence of active carbon as catalyst.

10 Claims, No Drawings

PROCESS FOR THE PRODUCTION OF ARYL CARBONATES

CROSS-REFERENCE TO RELATED APPLICATION

This Application is a Continuation-in-Part of application Ser. No. 07/780,494, filed Oct. 22, 1991, now abandoned.

This invention relates to a process for the production of carbonates containing aromatic ester groups by reaction of aromatic monohydroxy compounds with phosgene or chlorocarbonic acid esters of aromatic monohydroxy compounds with elimination of hydrogen chloride in the presence of active carbon.

Carbonates containing aromatic ester groups are suitable for the production of polycarbonates by the melt transesterification process and for the production of phenyl urethanes or are intermediates for the production of active substances in the pharmaceutical and plant protection fields.

It is known that aryl carbonates can be obtained by interfacial phosgenation (Schotten-Baumann reaction) of aromatic hydroxy compounds. The use of solvents and sodium hydroxide in this reaction is a disadvantage because partial saponification of phosgene or chlorocarbonic acid ester can occur under the effect of the sodium hydroxide. In either case, the large quantities of sodium chloride accumulating are a source of wastewater pollution. In addition, care has to be taken in recovery of the solvent to ensure effective protection of the environment.

Accordingly, it has been proposed to carry out a condensation reaction without using solvents in the presence of tetramethyl ammonium halides as catalysts (U.S. Pat. No. 2,837,555). However, the quantities of catalyst required for this purpose are relatively large. Quantities of 5 to 7% by weight catalyst, based on the quantity of phenol used, generally have to be used to obtain economic reaction rates. The reaction temperatures of 180 to 215° C. involve the danger of decomposition of the thermolabile tetramethyl ammonium halides. In addition, the catalyst has to be subsequently removed by washing with water which seriously complicates its recovery. In addition, far more than the stoichiometrically necessary quantity of phosgene is used. The yields of diphenyl carbonate amount to little more than 80% of the theoretical.

In another process (U.S. Pat. No. 3,234,263), diphenyl carbonates are obtained by heating phenyl chlorocarbonic acid esters in the presence of large quantities of alkali (alkaline earth) metal compounds and tertiary nitrogen bases as catalysts. However, this process has the disadvantage that high temperatures have to be applied to obtain even remotely economical reaction times. In this process, half the phosgene originally used is lost in the form of $CO_2$. In addition, the chlorocarbonic acid esters have to be synthesized in a separate preliminary process step.

DE-OS 2,447,348 relates to a process for the production of aryl carbonates in which phenols are phosgenated in the presence of heterocyclic nitrogen bases. Although this process is simpler than the processes mentioned above and gives better yields, the difficulties of clean removal of the catalyst remain. Accordingly, there is still a need for a simple continuous process.

It has now been found that carbonates containing aryl groups can be obtained very simply by reaction of phenols with phosgene or chlorocarbonic acid esters at elevated temperature in the presence of active carbon as catalyst.

Accordingly, the present invention relates to a process for the production of aryl carbonates by reaction of aromatic monohydroxy compounds with phosgene or chlorocarbonic acid esters of aromatic monohydroxy compounds, characterized in that the reaction is carried out at a temperature of 50 to 350° C. in the presence of active carbon as catalyst.

The process according to the invention has the major advantage that the catalyst can be removed very easily and no impurities are left in the crude reaction product. Working up is thus made considerably easier.

Aromatic monohydroxy compounds for the process according to the invention are those corresponding to the following formula $$Ar^1\text{—OH} \qquad (I)$$

in which
  $Ar^1$ represents phenyl, naphthyl, anthryl, phenanthryl, indanyl, tetrahydronaphthyl or the residue of a 5- or 6-membered aromatic heterocycle containing 1 or 2 hetero atoms from the group consisting of N, O and S; these isocyclic or heterocyclic residues may be substituted by 1 or 2 substituents from the group consisting of linear or branched $C_{1-4}$ alkyl, linear or branched $C_{1-4}$ alkoxy, phenyl, cyano and halogen and the heterocyclic residues may be attached to a fused benzene ring.

The linear or branched $C_{1-4}$ alkyl or $C_{1-4}$ alkoxy may be methyl, ethyl, propyl, isopropyl, butyl, isobutyl or methoxy, ethoxy, propoxy, isopropoxy, butoxy, isobutoxy, preferably methyl or methoxy. The halogen is, for example, fluorine, chlorine or bromine, preferably chlorine.

Preferred aromatic hydroxy compounds for the process according to the invention are those corresponding to the following formula $$Ar^2\text{—OH} \qquad (II)$$

in which
  $Ar^2$ represents phenyl or pyridyl which may be substituted by 1 or 2 substituents from the group consisting of linear or branched $C_{1-4}$ alkyl, linear or branched $C_{1-4}$ alkoxy, phenyl, cyano and halogen; in addition, the pyridyl may be attached to a fused benzene ring.

Particularly preferred aromatic hydroxy compounds for the process according to the invention are those corresponding to the following formula $$Ar^3\text{—OH} \qquad (III)$$

in which
  $Ar^3$ represents phenyl which may be substituted by 1 or 2 substituents from the group consisting of linear or branched $C_{1-4}$ alkyl, linear or branched $C_{1-4}$ alkoxy, phenyl, cyano and halogen and is preferably mono- or disubstituted by methyl, ethyl, propyl, isopropyl, methoxy, ethoxy, cyano, fluorine, chlorine and/or bromine. Examples of aromatic monohydroxy compounds are phenol, o-, m- and p-cresol, o-, m- and p-isopropylphenol, the corresponding halophenols or alkoxyphenols, such as p-chlorophenol or p-methoxyphenol; also monohydroxy compounds of naphthalene, anthracene and phenanthrene; and 4-hydroxypyridine and hydroxyquinoline.

The process according to the invention may be carried out both with phosgene and with chlorocarbonic acid esters of aromatic monohydroxy compounds. Where the process according to the invention is carried out with phosgene, the chlorocarbonic acid ester of the aromatic monohydroxy compound is initially formed and is reacted with more of the aromatic monohydroxy compound present in the reaction mixture to form the symmetrical diaryl carbonate of this aromatic monohydroxy compound. Where chlorocarbonic acid esters and an aromatic monohydroxy compound are used as starting materials, symmetrical or asymmetrical carbonates may be obtained, depending on the ester group in the chlorocarbonic acid ester. Symmetrical carbonates are obtained when the ester group present in the chlorocarbonic acid ester and the aromatic monohydroxy compound are the same. However, since symmetrical diaryl carbonates such as these can also be directly prepared from the aromatic monohydroxy compound by reaction with phosgene in the described manner, a procedure such as this has only minimal significance. However, the production of asymmetrical carbonates from an aromatic monohydroxy compound and a chlorocarbonic acid ester is of considerable significance. In this case, the ester group in the chlorocarbonic acid ester may also be an aromatic monohydroxy compound which falls within the scope of the disclosure for $Ar^1$—OH (I) or $AR^2$—OH (II) or $AR^3$—OH (III), but—in the context of the formation of asymmetrical diaryl carbonates—has a different substitution pattern from the monohydroxy compound used.

Accordingly, suitable chlorocarbonic acid esters for the process according to the invention are those corresponding to the following formula

$$R^1\text{—OCOCl} \quad\quad\quad (IV)$$

in which $R^1$ represents $Ar^1$.

Particularly suitable chlorocarbonic acid esters for the process according to the invention are those corresponding to the following formula

$$R^2\text{—OCOCl} \quad\quad\quad (V)$$

in which $R^2$ represents $Ar^2$.

Particularly preferred chlorocarbonic acid esters for the process according to the invention correspond to the following formula

$$R^3\text{—OCOCl} \quad\quad\quad (VI)$$

in which $R^3$ represents $Ar^3$. Where $Ar^1$ or $Ar^2$ or $Ar^3$ is disubstituted, the two substituents may be different substituents within the scope of the foregoing definition.

A key feature of the process according to the invention is that it is carried out in the presence of active carbon as catalyst. In the context of the invention, active carbon is understood to be activated carbon which can be produced from various carbon-yielding intermediates. The processes by which the carbon is converted into its active form can also be very different Processes such as these give active carbons which have BET surfaces of 200 to 3,000 m$^2$/g, preferably 300 to 2,000 m$^2$/g and, more preferably, 500 to 1,500 m$^2$/g. Suitable starting materials for the production of active carbons are, for example, sawdust and other wood waste, straw, various types of coal, such as bitumen coal or lignite, nutshells, mineral oil tars, lignin, polysaccharides, polyacrylonitrile, bones, peat. Coke products of lignites and mineral coals may also be used. Preferred starting materials are wood, cellulose, lignin, bitumen coal or lignite, peat or mineral coal coke.

The carbon-yielding intermediates mentioned above may be activated by various methods, for example by chemical activation with phosphoric acid or zinc chloride, by gas activation with steam, oxygen-containing gases or nitrous gases. The intermediates thus preactivated are then converted thermally, i.e. by coking, into active carbons for the process according to the invention. The production processes are known to the expert and, in exactly the same way as the various types of active carbon obtainable, are described in detail in the literature (see Ullmann's Encyclopedia of Industrial Chemistry, 5th Ed., Vol. A5 (1986), pages 124–140 and the literature cited therein).

Where suspended catalyst is used in stirred vessels or bubble columns, the active carbon catalysts mentioned are used in quantities of 0.5 to 100% by weight, preferably in quantities of 5 to 100% by weight and more preferably in quantities of 5 to 50% by weight, based on the quantity of monohydroxy compound used.

In the case of continuous operation in countercurrent or co-current or in the trickle phase using a fixed-bed catalyst, the catalyst loads used are from 0.1 to 20 g aromatic hydroxy compound per g catalyst per hour, preferably frpm 0.2 to 10 g•g$^{-1}$•h$^{-1}$ and, more preferably, from 0.2 to 5 g•g$^{-1}$•h$^{-1}$.

The active carbon used in discontinuous tests may be repeatedly used without purification providing the starting materials are not changed. Where the starting materials are changed, the active carbon is best purified by extraction with inert solvents of the type mentioned by way of example further below as reaction media or with alcohols, such as methanol, ethanol, isopropanol or butanol, with esters or amides of acetic acid or by treatment with superheated steam.

Where the process is carried out continuously the active carbon used may remain in the reaction for prolonged periods. Regeneration is generally not worthwhile, although it may be carried out by passing over superheated steam, optionally together with small quantities of air (approximately 0.1 to 20% by weight, based on the quantity of steam used), at a temperature of 150 to 800° C. or by passing over diluting gases, such as nitrogen, carbon monoxide or carbon dioxide, containing 0.01 to 5% by weight oxygen or by passing over carbon dioxide alone at a temperature of 200 to 800° C. The preferred regeneration temperature is in the range from 250 to 700° C. and, more particularly, in the range from 250 to 600° C.

The process according to the invention is carried out at a temperature in the range from 50 to 350° C., preferably at a temperature in the range from 100 to 300° C. and, more preferably, at a temperature in the range from 100 to 250° C. The temperature may be varied, preferably increased, within the range mentioned during the process according to the invention.

The process according to the invention is carried out under a pressure of 0.5 to 20 bar, preferably under a pressure of 0.8 to 10 bar and, more preferably, under a pressure of 1.0 to 5 bar. Maintaining a certain pressure is of secondary importance to the success of the process according to the invention.

The process according to the invention may be carried out in the presence of solvents. This is advisable where the starting products or end products have high melting points. Suitable solvents are solvents which are inert under the reaction conditions, including for example aliphatic and aromatic hydrocarbons, such as pentane, hexane, octane, decane, isononane, isooctane, cyclohexane, tert. butyl cyclohexane, cyclododecane, benzene, the isomeric xylenes, diethyl benzene, diisopropyl benzene, cumene, alkyl naphthalenes, biphenyl; halogenated hydrocarbons, such as dichloromethane, trichloroethylene, tetrachloroethylene, dichloroethane, dichlorohexane, chlorobenzene, dichlorobenzene, trichlorobenzene, chloronaphthalene, dichloronaphthalene; stable ethers, such as diphenyl ether or ditolyl ether. Other suitable inert solvents are known to the expert.

However, the process is preferably carried out in the melt, for example by introducing phosgene or a chlorocarbonic acid ester of the type mentioned into a suspension of active carbon in a melt of the aromatic monohydroxy compound and removing the catalyst by filtration on completion of the reaction. The phosgene escaping from the reaction vessel with the hydrogen chloride formed or escaping chlorocarbonic acid ester may be introduced into another suspension of active carbon in the aromatic monohydroxy compound; several other suspensions of the same type may be added on until the phosgene or the chlorocarbonic acid ester has been completely consumed, leaving only hydrogen chloride to escape. In this way, a carbonate synthesis may be industrially carried out by the process according to the invention, for example in a cascade of stirred tanks in which the gas stream moves in countercurrent to the stream of liquid.

In another preferred embodiment of the synthesis, a melt of the aromatic monohydroxy compound containing suspended active carbon catalyst is gassed with phosgene or phosgene/hydrochloride mixtures or with volatile chlorocarbonic acid esters in a continuous bubble column which may be combined with other bubble columns to form a cascade in which phosgene or chlorocarbonic acid ester and melt are reacted with one another in countercurrent, for example by introduction of fresh phosgene or fresh chlorocarbonic acid ester into the last column of a cascade from which the crude carbonate formed is then removed while the partly reacted stream of phosgene or chiorocarbonic acid ester containing hydrogen chloride is introduced into the columns still containing excess aromatic hydroxy compound in which more phosgene or chlorocarbonic acid ester is removed until only hydrogen chloride escapes from the first column of the cascade into which fresh aromatic hydroxy compound is introduced.

Another preferred embodiment is the co-current process in which aromatic hydroxy compound and phosgene or chlorocarbonic acid ester are applied in co-current, for example from above, to a catalyst filling arranged in a tube and hydrogen chloride and phosgenation products are removed at the bottom of the tube at the same point or at separate points.

In another preferred embodiment, which gives particularly favorable results, the reaction according to the invention is carried out in the trickle phase, i.e. the aromatic monohydroxy compound, in the form of a melt or solution, is applied from above to a bed of particulate active carbon and a stream of phosgene or volatile chlorocarbonic acid ester is introduced from below in countercurrent to this liquid stream. This embodiment is best carried out in a column which may even contain intermediate trays for improved distribution of the gas and liquid streams. In this trickle-phase embodiment, the gas stream escaping, from which phosgene and volatile chlorocarbonic acid ester have escaped and which already contains hydrogen chloride, may again be delivered to a following tricklephase column for further reaction in the manner described above.

In the described embodiments using the reactors mentioned, the two streams are best regulated in such a way that, for example at the bottom of a column, the aromatic monohydroxy compound is completely reacted and no more phosgene or chlorocarbonic acid ester escapes at the upper end. This may apply in the described manner to a single reactor and also to a cascade-like arrangement of several reactors.

In the countercurrent embodiment, particularly where substantially involatile chlorocarbonic acid esters are used, a gentle inert gas stream (for example carbon dioxide, nitrogen, natural gas, etc.) may optionally be passed downwards in countercurrent to blow out any hydrogen chloride formed.

The ratio between the reactants generally deviates only slightly from the equivalent quantities, i.e. the aromatic monohydroxy compound is generally reacted with phosgene in a molar ratio of 1.5–3:1 and preferably in a molar ratio of 1.8–2.5:1; in this case, the equivalent ratio is 2:1. Accordingly, the aromatic monohydroxy compound is reacted with a chlorocarbonic acid ester in a molar ratio of 0.5–1.5:1 and preferably in a molar ratio of 0.8–1.5:1; in this case, the molar ratio of 1:1 corresponds to the equivalent quantities.

These conditions may be expressed by the following reaction equations:

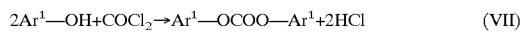

$$2Ar^1\text{—}OH + COCl_2 \rightarrow Ar^1\text{—}OCOO\text{—}Ar^1 + 2HCl \qquad (VII)$$

$$Ar^1\text{—}OH + ClCOO\text{—}R^1 \rightarrow Ar^1\text{—}OCOO\text{—}R^1 + HCl \qquad (VIII)$$

The substantial reaction of both reactants (aromatic monohydroxy compound and phosgene or chlorocarbonic acid ester) by only minimal deviation from the equivalent quantities may be controlled by adaptation of the molar ratios, the residence times on the catalyst and the reaction temperature, as known to the expert.

The crude aromatic carbonate obtained in this way is often very pure and, after the removal of residual hydrogen chloride or other volatile substances, may even be used in this form for many applications, more particularly because there is no need for further removal of catalyst. For more demanding applications, however, the carbonate may be further purified in the usual way by distillation or crystallization.

EXAMPLES

Example 1

In an approximately 4 cm diameter reaction tube, 200 g (2.13 mol) phenol were exposed to a gentle stream of phosgene flowing in through a frit at the bottom of the tube in the presence of 20 g powdered active carbon. After about 2 h at 150° C., the phenol conversion amounted to 24% while the selectivity to phenyl chlorocarbonic acid ester, was 82.25% and to diphenyl carbonate 17.75%.

Example 2

The procedure was as in Example 1, the phenol being exposed to phosgene gas for 2 h at 180° C. The phenol conversion amounted to 41%, the selectivity to phenyl chlorocarbonic acid ester was 24% and to diphenyl carbonate 76%.

Example 3

The reaction mixture of Example 2 was stirred for another 60 minutes at 180° C. in the absence of phosgene. The phenyl chlorocarbonic acid ester was converted with phenol still present into diphenyl carbonate; the selectivity to diphenyl carbonate was substantially quantitative.

Example 4

A heatable reaction tube approximately 30 cm long for a diameter of 2.8 cm was filled with approx. 90 g active carbon having a particle size of 4 mm (type VFTC 40/4 (shaped carbon) of the Bergwerksverband GmbH, Verkaufsgesellschaft für Teererzeugnisse, Duisburg) after which a stream of 50 g/h (0.53 mol) phenol was introduced from above while a stream of 30 g/h (0.30 mol) phosgene was introduced from below in countercurrent at 160° C. After 1 hour, a mixture showing a phenol conversion of 42%, a selectivity to diphenyl carbonate of 57% and a selectivity to phenyl chloroformic acid ester of 43% could be continuously removed at the foot of the column.

If this mixture was allowed to flow through a second catalyst filling of the type described above at a rate of 50 g/h and at a temperature of 170° C., the conversion into diphenyl carbonate was quantitative.

Example 5

A heatable reaction tube approx. 150 cm long for a diameter of 2.8 cm was filled with the active carbon of Example 4, after which a stream of phenol (40 g/h) was introduced from above while a stream of phosgene (30 g/h) was introduced in countercurrent from below, the phosgene being sprayed in approx. 30 cm above the lower end of the carbon filling. After about 6 h, a product of which more than 98% consisted of diphenyl carbonate flowed off from the lower end of the tube. The selectivity to diphenyl carbonate was substantially quantitative.

Example 6 (comparison):

Example 1 was repeated without the addition of active carbon. After 4 h at 175° C., the phenol conversion was <0.2%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of aryl carbonates comprising reacting an aromatic monohydroxy compound with at least one member selected from the group consisting of phosgene and chlorocarbonic acid ester of an aromatic monohydroxy compound at, a temperature of 50 to 350° C., in the presence of suspended active carbon catalyst, said catalyst being present in an amount of 5 to 100% relative to the weight of said monohydroxy compound.

2. The process of claim 1 wherein said powdered active carbon is suspended and is present in an amount of 5 to 100% relative to the weight of said phenol.

3. A process for the production of aryl carbonates comprising reacting an aromatic monohydroxy compound with at least one member selected from the group consisting of phosgene and chlorocarbonic acid ester of an aromatic monohydroxy compound at, a temperature of 150 to 180° C., in the presence of suspended active carbon catalyst, said catalyst being present in an amount of 5 to 100% relative to the weight of said monohydroxy compound.

4. The process of claim 3 wherein aromatic monohydroxy compound corresponds to the formula $$Ar^1\text{—OH}$$

in which $Ar^1$ represents phenyl, naphthyl, anthryl, phenanthryl, indanyl, tetrahydronaphthyl, the residue of a 5- or 6-membered aromatic heterocycle containing 1 or 2 hetero atoms selected from the group consisting of N, O, and S.

5. The process of claim 3 wherein aromatic hydroxy compound corresponds to the formula $$AR^2\text{—OH}$$

in which $AR^2$ represents phenyl or pyridyl.

6. The process of claim 3 wherein chaorocarbonic acid ester corresponds to the formula $$R^1\text{—OCOCl}$$

in which $R^1$ represents phenyl, naphthyl, anthryl, phenanthryl, indanyl, tetrahydronaphthyl, the residue of a 5- or 6-membered aromatic heterocycle containing 1 or 2 hetero atoms selected from the group consisting of N, O, and S, and wherein said $R^1$ may be substituted by 1 or 2 substituents selected from the group consisting of linear or branched $C_1$–$C_4$-alkyl, linear or branched $C_1$–$C_4$-alkoxy, phenyl, cyano and halogen and wherein said heterocyclic $R^1$ may be attached to a fused benzene ring.

7. The process of claim 3 wherein chlorocarbonic acid ester corresponds to the formula $$R^2\text{—OCOCl}$$

in which $R^2$ represents phenyl or pyridyl.

8. The process of claim 3 carried out under a pressure of 0.5 to 20 bar.

9. The process of claim 3 wherein said aromatic monohydroxy compound and phosgene are present in a molar ratio of 1.5–3:1 therebetween.

10. The process of claim 3 wherein said active carbon has a BET surface of 200 to 3,000 m²/g.

* * * * *